United States Patent
Carrion et al.

(10) Patent No.: US 6,555,096 B2
(45) Date of Patent: Apr. 29, 2003

(54) NAIL ENAMEL COMPOSITION CONTAINING A UREA-MODIFIED THIXOTROPIC AGENT IN A SOLVENT SYSTEM

(75) Inventors: Danuvio Carrion, Fords, NJ (US); Alan Farer, Kinnelon, NJ (US); Chris Frankfurt, Old Bridge, NJ (US)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/727,582

(22) Filed: Dec. 4, 2000

(65) Prior Publication Data

US 2002/0102222 A1 Aug. 1, 2002

(51) Int. Cl.$^7$ .......................... A61K 7/04; A61K 47/30; A61K 47/32
(52) U.S. Cl. .................... 424/61; 514/772.3; 514/772.4; 514/772.6; 514/781
(58) Field of Search .......................... 514/772.3, 772.4, 514/772.6, 781; 424/401, 61

(56) References Cited

U.S. PATENT DOCUMENTS

| | | |
|---|---|---|
| 2,173,755 A | 9/1939 | Fuller |
| 3,438,796 A | 4/1969 | Hanke |
| 4,166,110 A | 8/1979 | Isobe et al. |
| 4,179,304 A | 12/1979 | Rossomando |
| 4,283,324 A | 8/1981 | Duffy |
| 4,314,924 A * | 2/1982 | Haubennestel et al. 260/30.6 R |
| 4,410,570 A | 10/1983 | Kreuzer et al. |
| 4,434,010 A | 2/1984 | Ash |
| 4,712,571 A | 12/1987 | Remz et al. |
| 4,822,423 A * | 4/1989 | Soyama et al. ................ 106/5 |
| 4,838,648 A | 6/1989 | Phillips et al. |
| 4,897,261 A | 1/1990 | Yamazaki et al. |
| 4,930,866 A | 6/1990 | Berning et al. |
| 4,954,619 A | 9/1990 | Lang et al. |
| 5,071,639 A | 12/1991 | Soyama et al. |
| 5,093,108 A * | 3/1992 | Pappas et al. ................ 424/61 |
| 5,130,125 A | 7/1992 | Martin et al. |
| 5,145,671 A | 9/1992 | Castrogiovanni et al. |
| 5,171,363 A | 12/1992 | Phillips et al. |
| 5,174,996 A | 12/1992 | Weber et al. |
| 5,364,467 A | 11/1994 | Schmid et al. |
| 5,370,866 A | 12/1994 | Frankfurt et al. |
| 5,569,535 A | 10/1996 | Phillips et al. |
| 5,607,904 A | 3/1997 | Jarrett |
| 5,624,486 A | 4/1997 | Schmid et al. |
| 5,658,976 A | 8/1997 | Carpenter et al. |
| 5,688,494 A | 11/1997 | Graves et al. |
| 5,725,866 A | 3/1998 | Ramin |
| 5,766,335 A | 6/1998 | Bujard et al. |
| 6,156,325 A * | 12/2000 | Farer et al. .................. 424/401 |

FOREIGN PATENT DOCUMENTS

| | | |
|---|---|---|
| EP | 0 395 410 | 10/1990 |
| KR | 118766 * | 10/1997 |
| WO | WO 93/08237 | 4/1993 |
| WO | WO 00/27347 | 5/2000 |

OTHER PUBLICATIONS

"BYK Chemie Preliminary Data Sheet X4 for BYK®–410".
N. Haberle et al., "Right and Left Circular Polarizing Colorfilters Made From Crosslinkable Cholesteric LC–Silicones," *Institution of Electrical Engineers*, (1998).
R. Schmid et al., "Luster pigments with optically variable properties," (1997).
J. Hajas, "A Novel Liquid Rheology Additive for Solvent–Based and Solvent–Free Coatings," (1997).
M. Schlossman et al., "Advances in nail enamel technology," *J. Soc. Cosmet. Chem*, 43:331–337 (1992).
Robert Maurer et al., "Polarizing Color Filters Made From Cholesteric LC Silicones," *SID 90 Digest*, (1990).
H.J. Eberle et al., "Inverse angle dependence of the reflection colours of cholesteric polymeric liquid crystals mixed with pigments," (1989).
J. Pinsl et al., "Liquid Crystalline Polysiloxanes for Optical Write–Once Storage," *Journal of Molecular Electronics*, 3:9–13 (1987).
D. Makow, "Reflection and Transmission of Polymer Liquid–Crystal Coatings and Their Application to Decorative Arts and Stained Glass," *National Research Council of Canada*, 11:3 (1986).

* cited by examiner

Primary Examiner—Thurman K. Page
Assistant Examiner—S. Howard
(74) Attorney, Agent, or Firm—Finnegan, Henderson, Farabow, Garrett & Dunner, L.L.P.

(57) ABSTRACT

A nail enamel composition which contains, in a cosmetically acceptable solvent system containing diacetone alcohol and at least one additional solvent chosen from $C_1$–$C_6$ alkyl acetates and $C_1$–$C_6$ alkyl alcohols, at least one film-forming substance and at least one urea-modified thixotropic agent. The use of this thixotropic agent in the specific solvent system gives nail enamel compositions with higher gloss, high clarity, improved aesthetics in the bottle, excellent thixotropic properties, and improved application properties.

23 Claims, No Drawings

NAIL ENAMEL COMPOSITION CONTAINING A UREA-MODIFIED THIXOTROPIC AGENT IN A SOLVENT SYSTEM

The present invention relates to a nail enamel composition with at least one of improved thixotropic properties, higher gloss, and improved clarity in the bottle. More specifically, the invention relates to the use of a urea-modified compound as a thixotropic agent in combination with a specific solvent system in a nail enamel composition. The urea-modified compound and specific solvent system can provide at least one of thixotropic properties, high clarity, and high gloss that are improved compared to nail enamel compositions having the urea-modified compound and a solvent system other than that of the claimed invention.

Various nail enamel compositions are known in the art. Nail enamel compositions typically contain, in an organic solvent or mixture of solvents, film-forming ingredients, plasticizing ingredients, and colorants. Generally, the composition also contains a thixotropic agent, which may act to thicken the composition in order to allow better spreading on the nail. The thixotropic agent may also act to suspend the colorant.

The classic thixotropic agent used in the prior art is a bentonite clay. Aromatic organic solvents in particular may cause these clays to swell, thus providing a gel with good thixotropic properties, i.e., rendering the composition capable of passing from a gelled state to a liquid state simply by stirring and capable of going from liquid to gel after standing. A composition containing such a gel thus may exhibit relatively good dispersion stability without sedimentation or separation over a long Period. Further, such compositions may not require the vigorous shaking that other compositions often require after extended periods of storage.

The clay thixotropes, however, may produce cloudy suspensions, rendering the composition opaque and often giving it a more or less yellowish color inside the bottle, unpleasant to the eye. Although this opacity is generally masked by the presence of colorants and/or pigments in the composition, the use of the clay thixotropes may diminish gloss in the final formulated nail enamel product. Thus the need remains for a thixotrope-containing nail enamel composition that will not affect the glossiness of the nail enamel and yet will have sufficient thixotropic properties such that the stability of the composition is not compromised.

Accordingly, the present invention is drawn to a nail enamel composition containing, in a cosmetically acceptable solvent system comprising diacetone alcohol and at least one additional solvent chosen from $C_1$–$C_6$ alkyl acetates and $C_1$–$C_6$ alkyl alcohols; at least one film-forming substance; and at least one urea-modified thixotropic agent wherein the urea-modified thixotropic agent is a urea urethane having the following formula:

R—O—CO—NH—R'—NH—CO—NH—R"—NH—CO—NH—R'—NH—CO—OR

R is chosen from $C_nH_{2n+1}$— and $C_mH_{2m+1}(C_pH_{2p}O)_r$—; n is an integer having a value of from 4 to 22; m is an integer having a value of from 1 to 18; p is an integer having a value of from 2 to 4; and r is an integer having a value of from 1 to 10;

R' is chosen from

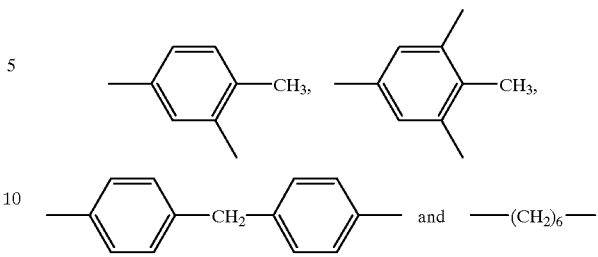

and R" is chosen from:

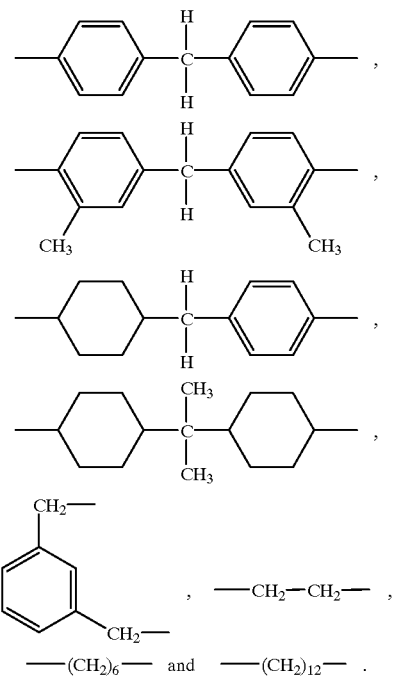

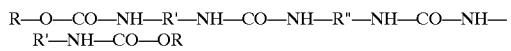

In one embodiment, the cosmetically acceptable solvent system comprises diacetone alcohol, at least one $C_1$–$C_6$ alkyl acetate and at least one $C_1$–$C_6$ alkyl alcohol.

The nail enamel composition of the invention may also contain a plasticizer and optionally a coloring agent.

The present inventors have discovered that the use of a urea-modified thixotropic agent with a solvent system comprising diacetone alcohol and at least one additional solvent chosen from $C_1$–$C_6$ alkyl acetates and $C_1$–$C_6$ alkyl alcohols, in place of the clay thixotropes of the prior art, may result in a clear suspension with improved gloss and improved clarity of suspension. In general, nail enamel compositions containing clay thixotropes only are difficult to process because their creation requires a great deal of high shear. Also, since the clay thixotropes are naturally occurring products, they can vary in quality and consistency. In contrast, the presently claimed compositions utilizing the urea-modified thixotrope in the claimed solvent system may be easy to produce consistently at optimum conditions because their creation may not require high shear processing.

Reference will now be made in detail to the embodiment(s) of the invention.

The presently claimed invention is drawn to a nail enamel composition which contains, in a cosmetically acceptable solvent system comprising diacetone alcohol and at least one additional solvent chosen from $C_1$–$C_6$ alkyl acetates and $C_1$–$C_6$ alkyl alcohols, at least one film-forming substance and at least one urea-modified thixotropic agent. The use of such a thixotropic agent with the claimed solvent system can give nail enamel compositions with at least one of higher gloss, high clarity, improved aesthetics in the bottle, excellent thixotropic properties, and improved application properties.

The urea-modified thixotropic agents used in the present invention are urea urethanes having the following formula:

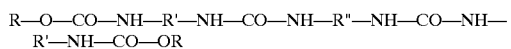

wherein

R is chosen from $C_nH_{2n+1}$— and $C_mH_{2m+1}(C_pH_{2p}O)_r$—; n is an integer having a value of from 4 to 22; m is an integer having a value of from 1 to 18; p is an integer having a value of from 2 to 4; and r is an integer having a value of from 1 to 10;

R' is chosen from

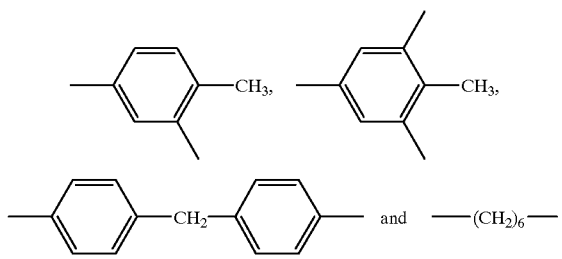

and R" is chosen from:

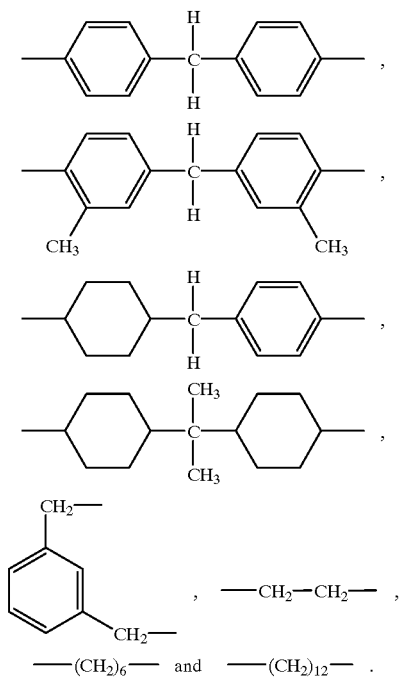

Such a urea-modified product can be purchased from BYK-Chemie in a dilute solution with N-methyl-pyrrolidone as solvent under the trade name of BYK®-410 and is generally described in U.S. Pat. No. 4,314,924, the disclosure of which is hereby incorporated by reference herein. In one embodiment, the at least one urea-modified thixotropic agent may be present in an amount of from about 0.05 to about 1.00% relative to the weight of the composition. In another embodiment, the at least one urea-modified thixotropic agent may be present in an amount of from about 0.25 to about 0.75% relative to the weight of the composition.

The nail enamel composition of the invention may contain at least one additional thixotropic agent, used in conjunction with the at least one urea-modified agent. When such an additional thixotropic agent is present, the composition may comprise from about 0.10 to about 0.30% of the at least one urea-modified thixotropic agent relative to the weight of the composition and up to about 1.0% of the additional thixotropic agent. The additional thixotropic agent(s) may be chosen from conventional silica and bentonite clay agents.

Film forming substances useful in the present invention include, but are not limited to, conventional film-forming agents such as nitrocellulose, other cellulose derivatives, such as cellulose acetate, cellulose acetate butyrate, and ethyl cellulose; polyesters; resins, such as polyurethane resins, alkyd resins, and polyvinyl resins such as polyvinyl acetate, polyvinyl chloride, polyvinylbutyrate; (meth)acrylic and vinyl copolymers such as styrene/butadiene copolymers, acrylate/vinyl acetate copolymers, acrylonitrile/butadiene copolymers, and ethylene/vinyl acetate copolymers.

In one embodiment, the primary film-forming agent may be nitrocellulose, which is known to give hardness and resistance to abrasion. If a second film-forming substance is present, this second film-forming substance may, for example, be chosen from cellulose acetate butyrate, polyesters, polyurethanes, and acrylates. In one embodiment, the film-forming substance may be present in an amount of from about 5% to about 20% by weight relative to the weight of the composition, for example, from about 10% to about 14%. Suitable modifiers for the primary film-forming agent include arylsulfonamide resins such as arylsulfonamide formaldehyde or epoxy resins.

The presently claimed composition also may contain at least one plasticizer. Plasticizers useful in the presently claimed nail enamel composition include plasticizers commonly employed in nail varnish compositions. These plasticizers encompass, but are not limited to, dibutyl phthalate, dioctyl phthalate, tricresyl phthalate, butyl phthalate, dibutoxy ethyl phthalate, diamylphthalate, tosyl amide, N-ethyl-tosyl amide, sucrose acetate isobutyrate, camphor, castor oil, citrate esters, glyceryl diesters, glyceryl triesters, tributyl phosphate, tri-phenyl phosphate, butyl glycolate, benzyl benzoate, butyl acetyl ricinoleate, butyl stearate, and dibutyl tartrate. In one embodiment, a plasticizer used in the present invention may be the mixture of acetyl tributyl citrate and N-ethyl tosyl amide. The plasticizer may, for example, be present in an amount of from about 3% to about 12% by weight relative to the weight of the composition.

The cosmetically acceptable solvent system of the present invention comprises diacetone alcohol and at least one additional solvent chosen from $C_1$–$C_6$ alkyl acetates and $C_1$–$C_6$ alkyl alcohols. In one embodiment, the $C_1$–$C_6$ alkyl acetates are chosen from ethyl acetate, propyl acetate, and butyl acetate. In another embodiment, the $C_1$–$C_6$ alkyl alcohols are chosen from ethanol, isopropanol, and butanol. Other cosmetically acceptable organic solvents which can be used in conjunction with the inventive solvent system include, but are not limited to, toluene; xylene; ketones such as acetone or methyl ethyl ketone; glycol ethers; alkanes such as hexane or heptane; -methyl pyrrolidone; and alkyl lactates. The solvent system of the invention, including any additional solvents, may be present, in one embodiment, in an amount of from about 40% to about 80% by weight relative to the weight of the composition, and, in another embodiment, from about 65% to about 78%.

The nail enamel composition of the invention may also contain at least one coloring agent. Conventional coloring agents can be used, and examples include inorganic pigments such as titanium dioxide, iron oxides, titanated mica, iron oxide coated mica, ultramarine, chromium oxide, chromium hydroxide, manganese violet, bismuth oxychloride, guanine, and aluminum; pearlescent materials; and organic coloring agents such as ferric ammonium ferrocyanide, and D&C Red Nos. 6, 7, 34, Blue No. 1, Violet No. 2, and Yellow No. 5.

The inorganic pigments may be surface-treated as is customary to prevent migration or striation. Silicones and polyethylenes are most often used as the coatings for inorganic pigments and thus may be used according to the present invention. Colorant materials may also include chips or powder of mica or diamonds in the nail composition. Also useful are specialty materials giving rise to two-tone color effects such as liquid crystal silicones or multi-lamellar metallic particulates, which generally can be mixed with pigments or dyes to obtain a broader spectrum of brilliant color and increased luminous reflectance. Such materials are described in, e.g., U.S. Pat. Nos. 3,438,796; 4,410,570; 4,434,010; 4,838,648; 4,930,866; 5,171,363; 5,364,467; 5,569,535; 5,607,904; 5,624,486; 5,658,976; 5,688,494; 5,766,335; N. Hätberle et al., "Right and Left Circular Polarizing Colorfilters made from Crosslinkable Cholesteric LC-Silicones," Conference Record of the 1991 International Display Research Conference (IEEE), pp. 57–59; R. Maurer et al., "Polarizing Color Filters made from Cholesteric LC-Silicones," SID 90 Digest (1990), pp. 110–113; H.-J. Eberle et al., "Inverse Angle Dependence of the Reflection Colours of Cholesteric Polymeric Liquid Crystals Mixed with Pigments," Liquid Crystals, 5(3), (1989), pp. 907–916; J. Pinsl et al., "Liquid Crystalline Polysiloxanes for Optical Once-Write Storage," J. Molec. Electr., Vol. 3 (1987), pp. 9–13; and D. Makow, "Reflection and Transmission of Polymer Liquid-Crystal Coatings and their Application to Decorative Arts and Stained Glass," Color Res. Applic. Vol. 11, No. 3, (1986), pp. 205–208, all of which are incorporated herein by reference in their entirety.

In one embodiment, the coloring agent may be present in the nail enamel composition in an amount up to about 5% by weight relative to the total weight of the composition. In another embodiment, the coloring agent is present in an amount of from 2% to 3% by weight.

The composition according to the invention may also include additives recognized by a person skilled in the art as being capable of incorporation into such a composition. For example, the composition may include at least one cosmetically active compound, which may be selected from vitamins, minerals, moisturizers, flavoring compounds, fragrances, masking agents, hardening agents such as silica and formaldehyde/glyoxal, UV absorbers, and fibers such as nylon and aramide fibers. Any art-recognized UV absorber can be used, both organic and inorganic. In one embodiment, inorganic UV absorbers include titanium dioxide and zinc oxide, both of which may be used in nanoparticulate form. In another embodiment organic UV absorbers include octocrylene, octylmethoxy cinnamate, and benzophenone.

Additional additive ingredients may include keratin and its derivatives, melanin, collagen, cystine, chitosan and its derivatives, ceramides, biotin, oligoelements, protein hydrolysates, and phospholipids.

A person skilled in the art can, without undue experimentation, select those optional additional compounds and/or their quantity, so that the advantageous properties of the composition according to the invention are not, or are not substantially, impaired by the inclusion of such additives.

The composition according to the invention may be prepared by a person skilled in the art on the basis of his or her general knowledge and according to the state of the art.

The composition according to the invention may be in the form of a product to be applied to the nails, such as a top coat, a base coat, or a pigmented nail lacquer or varnish.

The invention will be further clarified by the following examples, which are intended to be illustrative of the invention, but not limiting thereof.

EXAMPLE

Four compositions were formulated as set forth in the following table. The amounts listed are in grams.

| INGREDIENTS | COMPOSITIONS | | | |
| --- | --- | --- | --- | --- |
| | 1 | 2 | 3 | 4 |
| Ethyl Acetate | 24.80 | 22.80 | 24.40 | 23.80 |
| Butyl Acetate | 20.70 | 19.70 | 20.70 | 20.70 |
| Propyl Acetate | 9.70 | 9.70 | 9.70 | 9.70 |
| Nitrocellulose | 14.00 | 14.00 | 14.00 | 14.00 |
| Isopropyl Alcohol | 1.03 | 1.03 | 1.03 | 1.03 |
| Butyl Alcohol | 9.00 | 9.00 | 9.00 | 9.00 |
| Diacetone Alcohol | 4.50 | 4.50 | 4.50 | 4.50 |
| Acrylates Copolymer | 4.42 | 4.42 | 4.42 | 4.42 |
| Triphenyl Phosphate | 4.57 | 4.57 | 4.57 | 4.57 |
| Tosylamide Epoxy Resin | 2.40 | 2.40 | 2.40 | 2.40 |
| Polyester Resin | 2.40 | 2.40 | 2.40 | 2.40 |
| Acetyl Tributyl Citrate | 2.00 | 2.00 | 2.00 | 2.00 |
| Polyethylene Teraphthalate | — | 3.00 | — | — |
| D&C Red #6 Barium Lake | — | — | 0.30 | — |
| D&C Red #34 Calcium Lake | — | — | 0.10 | — |
| D&C Red #7 Calcium Lake | — | — | — | 0.10 |
| Mica (Splendid Violet) | — | — | — | 0.70 |
| Ferric Ammonium Ferrocyanide | — | — | — | 0.02 |
| Modified Urea-Urethane (BYK 410) | 0.50 | 0.50 | 0.50 | 0.50 |

Compositions 2, 3, and 4 are almost identical to inventive composition 1, but each contains a different colorant or additive.

Specifically, composition 2 is a translucent nail enamel containing polyethylene teraphthalate, commonly known as "glitter" and having a particle size ranging from 100 microns to 0.32 cm. This composition displayed improved particle suspension and bottle aesthetics when compared to a "classic" composition containing only a traditional clay-based thixotrope, and also when compared to a composition containing the urea-modified thixotrope of the invention but not the specifically claimed solvent system.

Thus, this example illustrates the ability of the present inventive compositions to suspend large particles without the presence of the traditional clay or silica thixotropes, i.e., using only the modified urea-urethane thixotrope and the solvent system comprising diacetone alcohol and at least one additional solvent chosen from $C_1$–$C_6$ alkyl acetates and $C_1$–$C_6$ alkyl alcohols.

Composition 3 contains two red pigments. Composition 4 contains pearlescent pigments. Like the other inventive composition, suspension, gloss, and stability were all improved for compositions 3 and 4 versus comparative compositions which did not contain the inventive solvent system.

What is claimed is:

1. A nail enamel composition comprising, in a cosmetically acceptable solvent comprising diacetone alcohol and at least one additional solvent chosen from $C_1$–$C_6$ alkyl acetates and $C_1$–$C_6$ alkyl alcohols:
   at least one film-forming substance and
   at least one urea-modified thixotropic agent, wherein said at least one urea-modified thixotropic agent is a urea urethane having the following formula:
   R—O—CO—NH—R'—NH—CO—NH—R"—NH—CO—NH—R'—NH—CO—OR
   wherein:
   R is chosen from $C_nH_{2n+1}$— and $C_mH_{2m+1}(C_pH_{2p}O)_r$—;
   n is an integer having a value of from 4 to 22;
   m is an integer having a value of from 1 to 18;
   p is an integer having a value of from 2 to 4;
   r is an integer having a value of from 1 to 10;
   R' is chosen from:

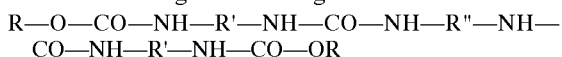

and R" is chosen from:

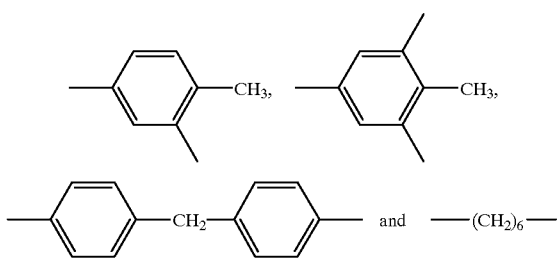

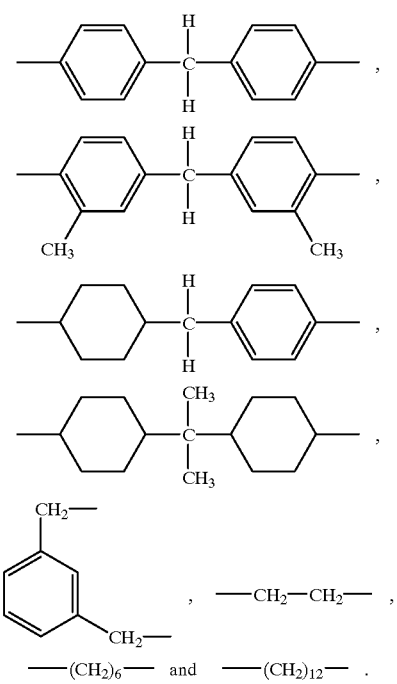

2. A nail enamel composition according to claim 1, said composition further comprising at least one plasticizer.

3. A nail enamel composition according to claim 1, said composition further comprising an additional film-forming substance.

4. A nail enamel composition according to claim 1, said composition further comprising at least one coloring agent.

5. A nail enamel composition according to claim 1, wherein said at least one film-forming substance is chosen from nitrocellulose, other celluloses derivatives, resins, polyesters, and (meth)acrylic and vinyl copolymers.

6. A nail enamel composition according to claim 5, wherein said cellulose derivatives are chosen from cellulose acetate, cellulose acetate butyrate, and ethyl cellulose, said resins are chosen from alkyd resins, polyvinyl resins, and polyurethane resins, and said (meth)acrylic and vinyl copolymers are chosen from acrylonitrile/butadiene copolymers, styrene/butadiene copolymers, acrylate/vinyl acetate copolymers, and ethylene/vinyl acetate copolymers.

7. A nail enamel composition according to claim 6, wherein said polyvinyl resins are chosen from polyvinyl acetate, polyvinyl chloride, and polyvinyl butyrate.

8. A nail enamel composition according to claim 5, wherein said at least one film-forming substance is nitrocellulose.

9. A nail enamel composition according to claim 3, wherein said additional film-forming substance is chosen from cellulose acetate butyrate, polyesters, polyurethanes, and acrylates.

10. A nail enamel composition according to claim 1, further comprising a modifier for said at least one film-forming substance, wherein said modifier is chosen from arylsulfonamide resins.

11. A nail enamel composition according to claim 1, wherein said $C_1$–$C_6$ alkyl acetates are chosen from ethyl acetate, propyl acetate, and butyl acetate.

12. A nail enamel composition according to claim 1, wherein said $C_1$–$C_6$ alkyl alcohols are chosen from ethanol, isopropanol, and butanol.

13. A nail enamel composition according to claim 2, wherein said at least one plasticizer is chosen from dibutyl phthalate, dioctyl phthalate, tricresyl phthalate, butyl phthalate, dibutoxy ethyl phthalate, diamylphthalate, tosyl amide, N-ethyltosylamide, sucrose acetate isobutyrate, camphor, castor oil, citrate ester, glyceryl diester, glyceryl triester, tri-phenyl phosphate, butyl glycolate, benzyl benzoate, tributyl phosphate, butyl acetyl ricinoleate, butyl stearate, and dibutyl tartrate.

14. A nail enamel composition according to claim 13, wherein said at least one plasticizer is chosen from acetyl tributyl citrate and N-ethyl tosylamide.

15. A nail enamel composition according to claim 1, wherein said cosmetically acceptable solvent system is present in an amount ranging from about 40% to about 80% by weight relative to the total weight of the composition.

16. A nail enamel composition according to claim 1, further comprising at least one additional solvent other than said cosmetically acceptable solvent system.

17. A nail enamel composition according to claim 16, wherein said at least one additional solvent is chosen from toluene, xylene, ketones, glycol ethers, alkanes, N-methyl pyrrolidone, and alkyl lactates.

18. A nail enamel composition according to claim 16, wherein said at least one additional solvent and said cosmetically acceptable solvent system are present in a combined amount ranging from about 40% to about 80% by weight relative to the total weight of the composition.

19. A nail enamel composition according to claim 1, wherein said at least one film-forming substance is present in an amount ranging from about 5% to about 20% by weight relative to the total weight of the composition.

20. A nail enamel composition according to claim 1, wherein said at least one plasticizer is present in an amount ranging from about 3% to about 12% by weight relative to the total weight of the composition.

21. A nail enamel composition according to claim 1, wherein said at least one urea-modified thixotropic agent is present in an amount ranging from about 0.05% to about 1.00% relative to the total weight of the composition.

22. A nail enamel composition according to claim 21, wherein said at least one urea-modified thixotropic agent is present in an amount ranging from about 0.25% to about 0.75% relative to the total weight of the composition.

23. A nail enamel composition according to claim 1, wherein said composition further comprises at least one cosmetically active compound selected from vitamins, minerals, moisturizers, flavoring agents, fragrances, masking agents, hardening agents, UV absorbers and fibers.

* * * * *